United States Patent
Kamentsky et al.

[11] Patent Number: 5,885,840
[45] Date of Patent: Mar. 23, 1999

[54] MULTIPLE ASSAYS OF CELL SPECIMENS

[75] Inventors: Louis A. Kamentsky, Boston; Douglas E. Burger, Stoughton; Russell J. Gershman, Lexington; Lee D. Kamentsky, Arlington; Ed Luther, Wilmington, all of Mass.

[73] Assignee: Compucyte Corp., Cambridge, Mass.

[21] Appl. No.: 798,488

[22] Filed: Feb. 10, 1997

[51] Int. Cl.[6] .................................................. G01N 33/48
[52] U.S. Cl. ......................... 436/63; 436/164; 436/172; 435/4; 435/6; 435/29; 356/73; 356/317; 356/318; 382/133; 702/21
[58] Field of Search .......................... 436/63, 164, 172; 435/4, 6, 29, 30, 34; 364/413.01, 413.08; 935/76, 77; 356/73, 300, 317, 318; 382/133; 702/19, 21

[56] References Cited

U.S. PATENT DOCUMENTS

| | | | |
|---|---|---|---|
| 4,647,531 | 3/1987 | Kamentsky | 435/7.24 |
| 5,072,382 | 12/1991 | Kamentsky | 382/133 |
| 5,427,910 | 6/1995 | Kamentsky et al. | 435/6 |

OTHER PUBLICATIONS

Kamentsky et al. "Microscope–Based Multiparameter Laser Scanning Cytometer . . . " *Cytometry*, vol. 12, pp. 381–387, 1991.

Kamentsky et al. "Slide–Based Laser Scanning Cyto–metry." *Acta Cytologica*, vol. 41, No. 1, pp. 123–143, Jan.–Feb. 1997.

*Primary Examiner*—Maureen M. Wallenhorst
*Attorney, Agent, or Firm*—Graham & James LLP

[57] ABSTRACT

A method for increasing the accuracy and the types of data measurements of laser scanned dye stained cells, in a single sample, by means of multiple assays, utilizing cell positions as a factor in merging data measurements. Change in lasers, use of different cell dye stains and different treating reagents provide additional data regarding cells of the sample and fixing of cell positions in the first assay permits merging of the data obtained in subsequent assays.

16 Claims, 9 Drawing Sheets

MULTIPLE ASSAYS OF CELL SPECIMENS

FIELD OF THE INVENTION

This invention relates to the scanning of fluorescent dyed cells in a cell sample, by means of a laser scanning cytometer and particularly to multiple scans of the same cell sample.

BACKGROUND OF THE INVENTION

A technique using fluorescent dyes for characterizing cells by flow cytometry (FCM) has been of considerable utility in immunohematology and cell biology. Another technique known as laser scanning cytometry (LSCM) has been developed to automatically measure laser excited fluorescence at multiple wavelengths and light scatter from cells on stationery slides (as opposed to a flow as in FCM) that have been treated with one or more fluorescent dyes in order to rapidly determine multiple cellular constituents and other features of the cells.

A laser scanning cytometer can use the methods perfected for FCM and has been shown to provide data equivalent to FCM for DNA analysis of aneuploid specimens, for immunophenotyping, and for analysis of cell proliferation and apoptosis. Because it is microscope based and measures cells on a slide and not in a flow chamber (as used in FCM), records position of each cell on the slide, and has higher resolution, it provides a number of benefits that may make it more suitable for pathology laboratories than FCM.

FCM has used fluorescent dyes to quantify cell constituents because fluorescence emissions are directly proportional to the mass of the constituent stained by the dye, if dye concentrations are low. Additionally, light scatter which has been useful to characterize cellular size and granularity occurs at a different wavelength than fluorescence and is easily separated from it in FCM. Automated fluorescence image analysis (FIA) in which a specimen is illuminated by an arc lamp or laser light source and is imaged at one or more wavelengths, using a CCD camera, has also been characterized for use in cell analysis.

The technologies of FIA, FCM and LSCM can be utilized to quantify cell constituents using fluorescence. Two of these, FCM and LSCM measure scatter as well as fluorescence. FIA, FCM, and LSCM each automatically measure fluorescence at multiple wavelengths of cells that have been treated with one or more fluorescent dyes in order to rapidly assay multiple cellular constituents. In FCM and LSCM, fluorescence and scatter result from interaction of the cells with a laser beam comparable in spot size to the cell. The laser optics is designed to produce a large depth of field with nearly collimated excitation to achieve accurate constituent measurements independent of cell position in the FCM stream or LSCM slide focus. In FIA the cells are uniformly illuminated, preferably by a mercury or xenon arc epi-illuminator. Fluorescence is imaged at high resolution and low depth of focus by a sensitive CCD camera. Commercial FIA, FCM and LSCM instruments provide feature values, for each event found, in standardized format computer list mode files.

In LSCM, the cells are measured and retained on a solid support such as a slide. In FCM, cells flow past the laser in a flow of cells which end in a waste container. The LSCM slide position and laser beam are moved under computer control to excite the cells. Since the position of the slide and laser beam is known to the computer, cell position on the slide is a measurement feature of LSCM but cell position cannot be a feature of FCM.

In LSCM, interactions of each cell and the laser are measured and recorded many times in a two dimensional pattern and features computed from these inter-actions are derived. In contrast, in FCM, properties of a single analog pulse are recorded as each cell flows past the laser focus.

With LSCM, because cells are prepared and measured on a slide, it is not necessary to provide single cell or nuclei only cell suspensions. Touch or needle biopsy specimens can be made as imprints or smears or tissue can be measured directly. Cytoplasmic as well as nuclear constituents can be characterized and centrifugations are not required and fewer cells may be lost. Preparations requiring amplification or specific fixatives can be employed without agglutination or cell clumping. The complete area encompassing a specimen is able to be scanned to allow all cells in a small specimen to be measured.

Since the absolute position on the slide of each measured cell's coordinates are recorded in the cell's list of features, the position feature can be used to relocate cells for visual observation or CCD camera image capture. Images may be included in reports or used for high resolution analysis of selected cells. Additionally, cells may be observed and categorized and their category used as values of a category feature for subsequent data analysis. Conversely, cells may be visually located and features of observed cells displayed. The position feature can be treated and displayed as any other feature and used for quality control of staining by displaying a fluorescence feature versus X or Y position.

The LSC™ laser scanning cytometer, available from CompuCyte Corporation, makes measurements on each cell at 0.5 micron spatial intervals. Features can be computed such as area, perimeter, the peak value found in the array, and texture, all of which give additional information useful in characterizing cells with fewer dyes and sensors. Constituents that are localized to regions of the cell such as probe spots in fluorescence in situ hybridization (FISH) preparations can be independently characterized yielding other features not obtainable with FCM. The total fluorescence, area, and peak fluorescence of the individual probe spots are used as laser scanning cytometer features allowing the laser scanning cytometer to more accurately count probe spots in cells of FISH specimens.

Cell contouring, i.e., outlining of the cell, is effected by presetting sensors to measure individual position pixel fluorescence values within the cell and to locate pixel positions within the cell where there is a predetermined drop-off of fluorescence value (threshhold value). A position having the predetermined drop-off is a boundary position, with the sum of such sites working to contour the cell.

A list of feature values is computed and stored in a PC computer disk data file for each cell found by the laserscanning cytometer. This list contains the following feature values:

For the sensor used for contouring:
1) The integrated value (the corrected sum of the pixel values in the data contour) equivalent to the FCM constituent value,
2) The peak-value within the data contour,
3) The area of the thresholding contour,
4) The perimeter of the thresholding contour,
5) The absolute slide position of the event's peak value,
6) The computer clock time when the event was measured,
7) The number of probe spots within the cell's data contour for FISH specimens, 8) An annotation feature which the user adds as cells are relocated and visually observed, 9) The structure of the data within the contour is analyzed to determine if the event represents a single or a multiple cell. Multiple cell events are tagged.

For every other sensor:

1) The integrated value,

2) The peak value within the data contour.

For every probe spot during FISH applications:

1) The integrated value of all pixels in the probe contour,

2) The area of the probe contour,

3) The distance to the nearest probe spot.

As each specimen is run, the PC computer monitor screen shows a series of windows. Any number of windows containing scatter diagrams of any two features, or histograms of one feature can be displayed. These scattergrams or histograms can be related to the gating region of any other scattergrams or histograms so as to only display cells within the parent display's gating region. Any number of gating regions can be drawn using a mouse. In this way complex relationships involving any sets of features can be developed and used to display subsequent scattergrams or histograms compute a variety of statistics of cells within a region, including sub-population counts and distribution statistics, or to select events for relocation and visualization.

In both FCM and LSCM, it is desirable to simultaneously measure as many constitutents of individual cells as possible. For example, it is desirable to measure the total DNA of each cell simultaneously with two specific DNA sequences in which two fluorescence in situ hybridization probes are each bound to different fluorescent molecules or to simultaneously characterize DNA per cell, cell proliferation, and cell apoptosis. The number of constitutents that can be measured is limited since each laser used emits a single wavelength and can excite dyes to fluoresce only at wavelengths longer in wavelength than the excitation wavelength. Additionally, the excitation bands of many dyes are broad and have grossly different emission intensities and do not allow distinguishing multiple constituents, each stained with different constituent specific dyes. For example, the dye propidium iodide (PI), used to stain DNA, is used in LSCM for both finding and associating each cell's fluoresence digital data for analysis, as well as determining total DNA values per cell. PI is excited by an Argon ion laser and has a broad spectral distribution which does not allow any other dye excited by an Argon ion laser and emitting fluoresence at longer wavelengths than PI to be measured simultaneously with PI, limiting the number of cell constituents that can be measured. Another laser other than the Argon ion laser such as a red light emitting HeNe laser can be used to excite the fluoresence of longer wavelength emitting dyes such as CY3 and CY5 that can be conjugated to antibodies that will bind to specific DNA sequences or specific cell proteins. However, both lasers can not be used simultaneously in LSCM because the direct red light from the HeNe laser will interfere with the measurement of the Argon ion excited dyes since its wavelength is close the Argon ion excited dyes emission wavelength, and the Argon ion excited dyes emission will overlap the emission of the red laser excited dyes. It has therefore not been possible to distinguish more than one additional constituent when using dyes such as PI in a single LSCM assay.

SUMMARY OF THE INVENTION

Generally the present invention comprises a method for scanning a cell sample for analysis, multiple times, with different examination parameters, with the results of the multiple scannings being merged into a single profile of scanning results for individual cells in the sample, said method comprising the steps of:

a) utilizing scanning means to examine the cell sample with initial examination parameters, while determining and recording the position of individual cells relative to the scanning means;

b) utilizing the scanning means to examine the cell sample for each of the remainder of the multiple times and determining and recording the position of the individual cells relative to the scanning means during each of said remainder of the multiple times;

c) using the recorded cell position of the individual cells from each of multiple examinations as a key to merge results obtained for individual cells having positions within predetermined deviation values. It is preferred, though not necessary, that the key also includes positions outside of predetermined overlapping distance values from adjacent cells.

In a specific embodiment of the present invention the major deficiency of the prior art can be overcome by using the capability of the laser scanning cytometer to record the exact position of each cell along with other features. In this embodiment, a specimen is stained with both Argon ion excited dyes such as PI and fluorescein, which cannot be excited by the red HeNe emission, and red HeNe excited dyes that will not be excited by Argon ion laser emission. The specimen is assayed twice, the first time with the Argon ion laser recording the measurements from the Argon ion laser excited dyes as well as the position of each cell. The specimen is then assayed a second time using the HeNe laser as an excitation source. The data from the two assays is merged using each cell's position as the merge key yielding non interfering constituent measurement data. Alternatively, the laser scanning cytometer can be programmed to scan each area of the slide twice, alternating the laser used for excitation used in the scan area and combine data from both passes, using the data from one of the passes to associate the data representing each cell. A third alternative to be described, is to use multiple assays but to change the dyes used to stain the cells between assays, again combining data from each assay based on cell position.

It is an object of the present invention to provide a method for scanning a single cell sample for analysis, multiple times, with different search or examination parameters, with results being merged into a single file for the individual cells.

It is another object of the present invention to effect such merging of disparate cell data by means of LSCM and by initially recording and using specific cell position as a correlation or sort key.

It is a further object of the present invention to provide a useful means to permit staining and effective analysis of a cell specimen with dyes excited by different lasers and particularly with PI and red laser excited dyes.

It is yet a further object of the present invention to provide a means to permit scanning of a specimen with a short wavelength laser with recordation of the position and contour surrounding PI fluorescence of each cell found with the cell's DNA value.

It is a still further object of the present invention to assay a scan strip a second time with a longer wavelength laser, and recording the fluorescence values of the red laser excited dyes within a contour approximately equal in position and size for that found for each cell in the first assay.

These and other features, objects and advantages of the present invention will become more evident from the following discussion and the drawings in which:

DETAILED DESCRIPTION OF THE INVENTION

Prior art software, developed for laser scanning cytometers, allows generation of data regarding scanned cells under conditions of various parameters, as described, such as with use of different dyes (and compatible excitation lasers). One set of the values obtained in a list of feature values of data from a laser scanning cytometer is that of cell position in the scan. In accordance with the present invention, the cell position in each of the scans is utilized as a key to merge data obtained from the individual scans to provide cumulative data for the specific individual cells, a feature not possible with single assays or even with normal multiple assays. In a first scan, individual cell positions (X-axis, Y-axis and scan mirror position) are measured and recorded. Means are provided in the scanning device to permit exact relocation of the sample relative to the scanner, e.g., a sample slide relocatable slide holder. The sample is then relocated for a second scan and, in the second scan, individual cell positions are again measured and recorded. Data files for each of the scans are merged for individual cells which are in the same position and within a pre-selected deviation position value and which are also distant from a neighboring cell by at least a pre-selected overlapping position value. The merged data files are then considered to be characteristic fuller profiles of the individual cells which fulfill the merge position parameters.

In accordance with the present invention, after merging the two files (representing the results of each assay), provide a sensitive measure of multiple cell constituents, much less affected by irrelevant factors such as autofluorescence.

Slides can be rerun and feature values from each run can be combined for each cell on the slide using position as the merge key to create multi-run feature sets. The slide may be restrained or the laser excitation wavelength may be changed between runs. The cells may be treated between runs to measure and record kinetic properties of heterogeneous populations or to measure per cell differences between a control and an analyte. Multiple scans may be made with adjustment of the computational parameters of the cytometer such as by changing the gain of sensors to determine both large and small amounts of a constituent with great dynamic range using limited dynamic range sensor amplifiers, or by changing the size of data contours to better measure cellular constituent distributions. The specimen can also be assayed without staining or with a control stain (irrelevant antibody conjugated to a fluorescent dye) then assayed after staining the specimen.

In accordance with the present invention the computer controlled laser scanning cytometer is provided with software control and instructions whereby either independent runs are used for generating data lists or data runs depending on data from the first run to establish cell locations and data contours.

The controlling software for the laser scanning cytometer is designed to operate:

1) based on merging the values of data features for each cell in the same position on the slide during each of multiple assays; or 2) based on establishing the positions and the extent (the data contour for each cell) during a scan strip, then changing the laser excitation, sensors used and computational parameters and rescanning the same specimen strip, using that position and extent for each cell found to determine new values for the features.

Two methods are useful in providing such features, one for each of independent assays and dependent assays, as will be described.

DETAILED DESCRIPTION OF THE DRAWINGS AND THE PREFERRED EMBODIMENTS

Figure 1:
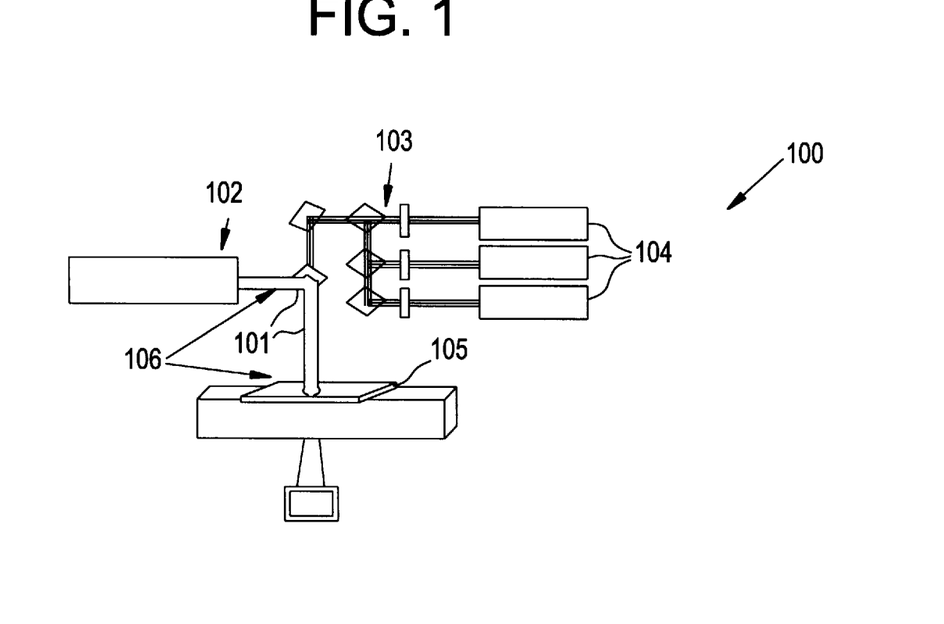
FIG. 1 schematically depicts laser scanning cytometry (LSCM)

An LSCM system 100, as illustrated in an overview form in FIG. 1, is utilized to quantify cell constituents using fluorescence to measure scatter as well as fluorescence. The LSCM automatically measures fluorescence at multiple wavelengths of cells that have been treated with one or more fluorescent dyes in order to rapidly assay multiple cellular constituents. Fluorescence and scatter result from interaction of the cells with a laser beam 101 comparable in spot size to the cell. The laser optics 102 is designed to produce a large depth of field with nearly collimated excitation to achieve accurate constituent measurements independent of cell position in the slide focus. Wavelength band pass filters 103 are used to isolate the fluorescence to each of multiple photomultipliers 104.

In LSCM, the cells are measured and retained on a solid support such as a slide 105 and the slide position and laser beam 101 are moved under computer control 106 to excite the cells. Since the position of the slide and laser beam is known to the computer, cell position on the slide is a measurement feature. Interactions of each cell and the laser beam are measured and recorded many times in a two dimensional pattern and features computed from these interactions are derived.

Figure 2:
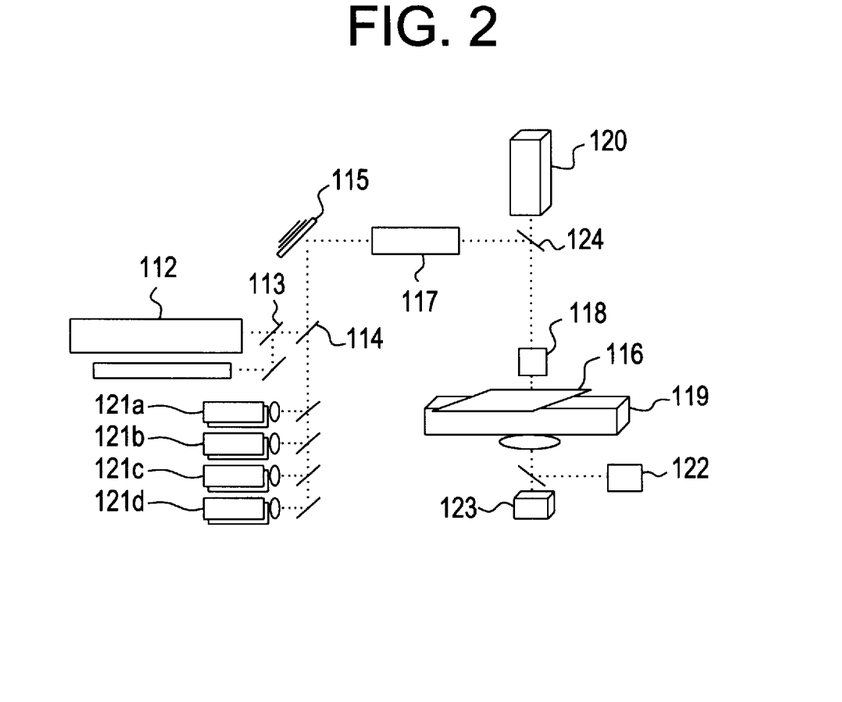
FIG. 2 schematically depicts component and operation parts of a laser scanning cytometer commercially available as an LSC™ cytometer from CompuCyte Corp.

A block diagram of the LSC™ laser scanning cytometer from CompuCyte Corp., is shown in FIG. 2. The beams from an Argon ion and a HeNe laser 112 are combined at a dichroic mirror 113 and steered to a second dichroic mirror 114 designed to reflect the laser wavelengths and to transmit other wavelengths. Each laser's output level is controlled by the laserscanning cytometer computer. The combined beam is steered to a computer controlled scanning mirror 115 producing a saw tooth motion at a nominal rate of 350 Hz creating a line scan at the microscope slide 116. After passing through a scan lens 117, the beam enters the epiillumination port of a standard Olympus BX50 microscope and is imaged by the objective lens 118 on to the focal plane at the specimen, producing a 10 $\mu$ diameter spot over 685 $\mu$ using a 10× objective, a 5 $\mu$ diameter spot over 342 $\mu$ using a 20× objective, or a 2.5 $\mu$ diameter spot over 171 $\mu$ using a 40× objective. The specimen slide 116 is mounted in a holder on the stage of a computer controlled stepper motor stage 119 equipped with absolute position sensors. Nominal stage motion during runs is perpendicular to the scan at 0.5$\mu$ movements per scan line, followed by a larger stage motion in the scan direction after a series of scan strips. Light scattered by cells is imaged by the microscope's condenser lens to an assembly containing a beam blocking bar and solid state sensor 122. This assembly's position is computer controlled to move outside the microscope's bright field source 123 so that the microscope's bright field source can be used for viewing objects through the eyepiece or with the CCD camera 120. Fluorescent energy is collected by the objective lens, reflected by a partially silvered mirror 124 to allow a CCD camera to image cells, and steered through the scan lens and to the scanning mirror 115. It then passes through a series of dichroic mirrors and optical interference filters to up to 4 photomultipliers 121*a–d*, each detecting a specific fluorescence wavelength range.

Four sensor signals are simultaneously digitized at 625,000 Hz, corresponding -nominally to 0.5 $\mu$ spatial intervals along the scan. With the 0.5 $\mu$ stage movement, sampling is at 0.5 $\mu$ intervals in both X and Y directions. The sensors are digitized by an analog to digital converter to 12 bit digital values. These digital values are stored directly in 4 of 8 banks of memory in a PC computer. Data acquisition takes place into 4 data banks while data is analyzed in the other 4 data banks. Data bank sets are interchanged after each scan strip to allow the laserscanning cytometer to simultaneously acquire and analyze data. If required, the user can set the laser scanning cytometer software to sum sensor digitized values from two or more successive scans into each memory location representing the data along each scan line, effectively increasing digitization precision and instrument sensitivity.

Figure 3:
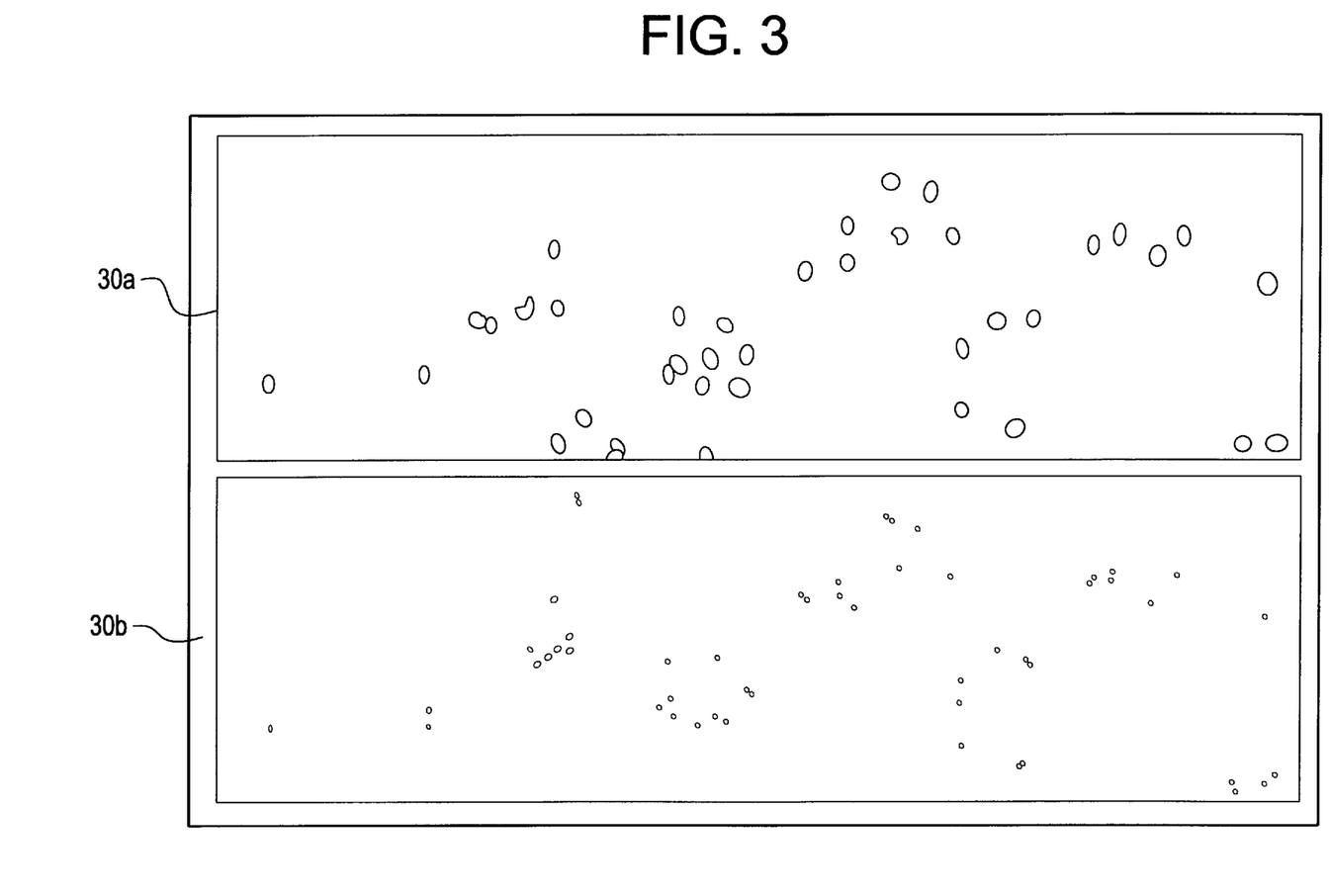
FIG. 3 is a reproduction of an actual scan of cells stained with red fluorescent dye and green fluorescent dye and the fluorescing thereof with Argon 104 lasers.

Shown in FIG. 3 are scan data displays of the red fluorescence 30*a* and green fluorescence sensors 30*b* respectively after a scan strip. A specimen slide of male and female lymphocytes stained with propidium iodide (PI) and hybridized with an X chromosomal specific DNA probe conjugated to fluorescein isothyocynate (FITC) was run. The values at each pixel location are shown with a level of brightness at that position proportional to the pixel's value. A 40× objective and 2.5 $\mu$ spot size was used in this run. The data is first segmented in order to associate it with isolated events. The user sets a contouring threshold at some intensity level using one of the sensors.

Figure 4:
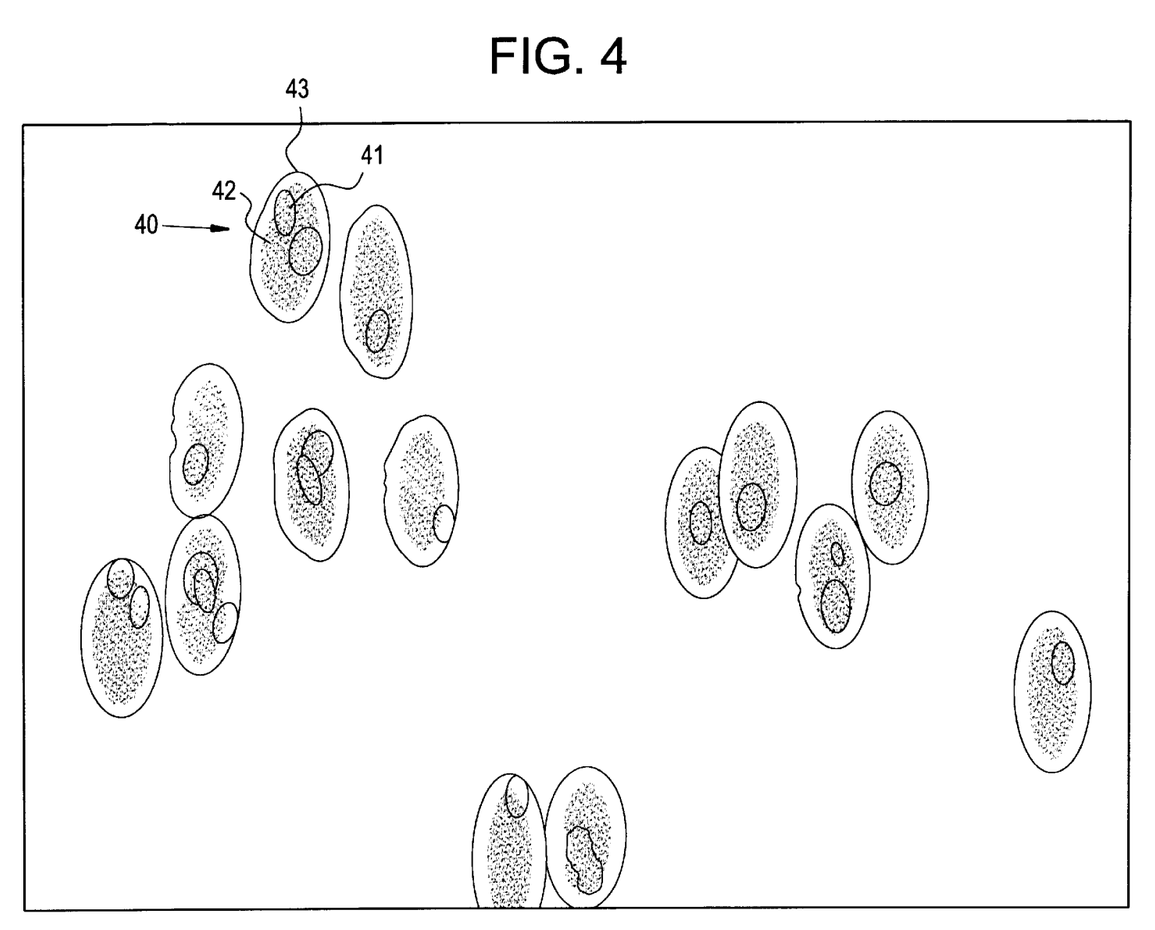
FIG. 4 illustrates typical cell contouring with a laser scanning cytometer.

In FIG. 4, in which the first inner contour 41 around the cell image 40 is the threshold contour, the red fluorescence of PI stained lymphocytes was used as the contouring threshold parameter. The shape of the laser excitation beam is Gaussian and cell images are generated in which the data for each cell does not end abruptly at the threshold contour edge. For this reason, a second contour 42, a fixed number of pixels outside the threshold contour is used to define event data. The pixels within this data contour are used to compute the cell's total or integrated fluorescence and scatter values. By increasing the spacing between these contours, the user can set a higher threshold to better isolate cell events.

To accurately determine cell constituent values in the presence of background fluorescence or scatter, it is necessary to establish a base background value for each cell for each sensor. This can be done on a slide by slide basis with one background level per sensor determined for each run or dynamically with the background level determined independently for each cell. As shown in FIG. 4, if the user chooses to use a dynamic background determination, a third contour set 43 some number of pixels outside the second contour is drawn. A function of the pixel values along this contour is used to determine the cell's back-ground which is subtracted from the values used to determine integrated value of total fluorescence or scatter. The user can select these background algorithms to determine either minimum or average values along the background contour. They are designed to reject the cell's background determination and either reject the cell, or use the previous cell's background if the data along the background contour does not meet specific regularity criteria. If FISH preparations or other specimens are run containing localized constituents that can be independently stained and sensed, the laser scanning cytometer can draw a second set of contours within the cell contours based on this second sensor signal.

Figure 5:
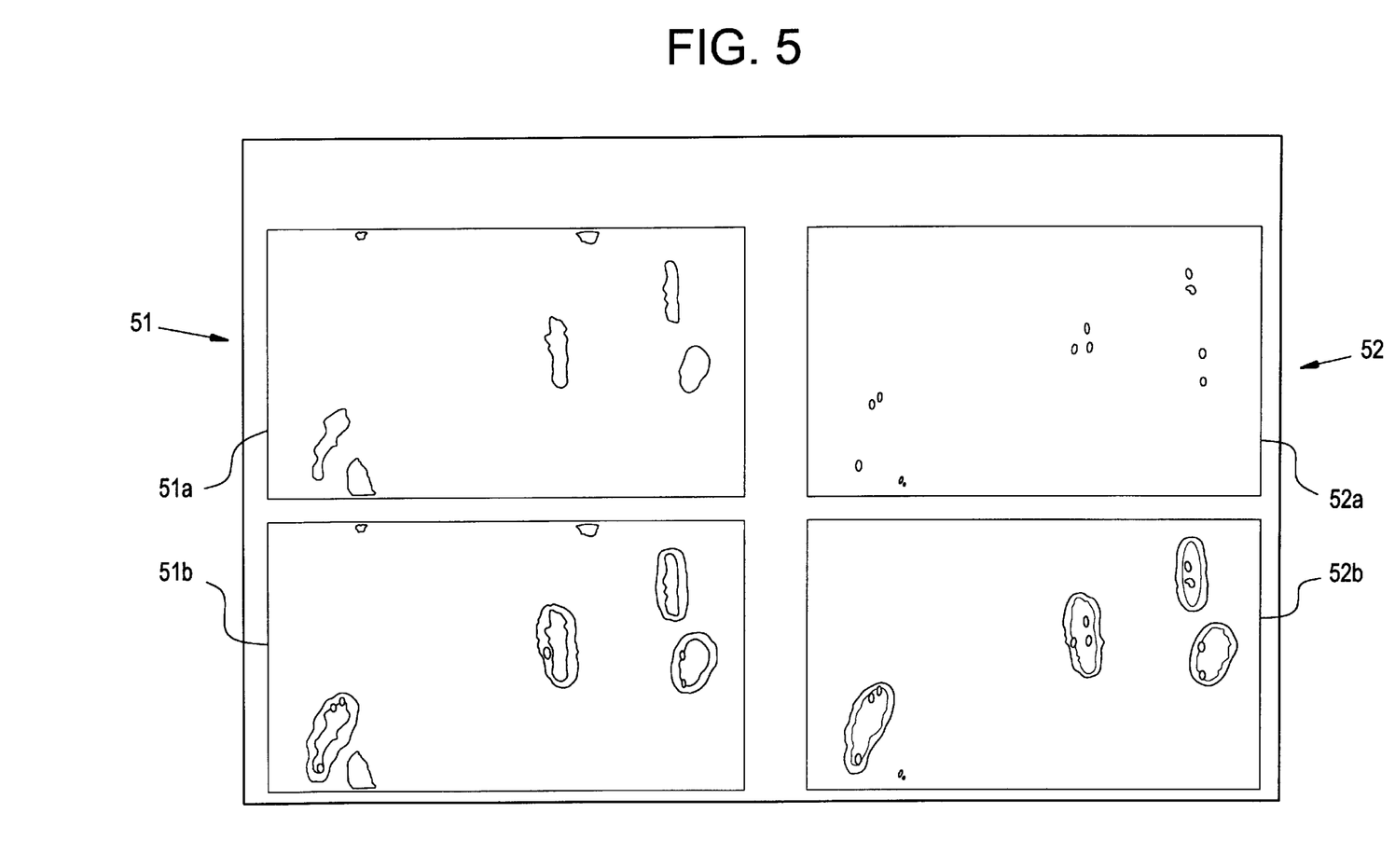
FIG. 5 shows sensor and contouring data from a run of mixed diploid and triploid fibroblasts stained with PI and hybridized with a FISH probe.

FIG. 5 shows sensor data from a run of mixed diploid and triploid fibroblasts stained with PI and hybridized with a FISH probe to chromosome 8 conjugated to Spectrum Green (Vysis, Downers Grove, Ill.). Laser scan images of the red sensor data 51, measuring PI nuclear fluorescence, and the green sensor data 52, measuring probe Spectrum Green fluorescence, are shown without 51*a*, 52*a* and with dual contouring 51*b*, 52*b*. The lower set of images shows both contours surrounding the PI stained nuclei and contours surrounding the FITC tagged DNA probe spots.

Figure 6:
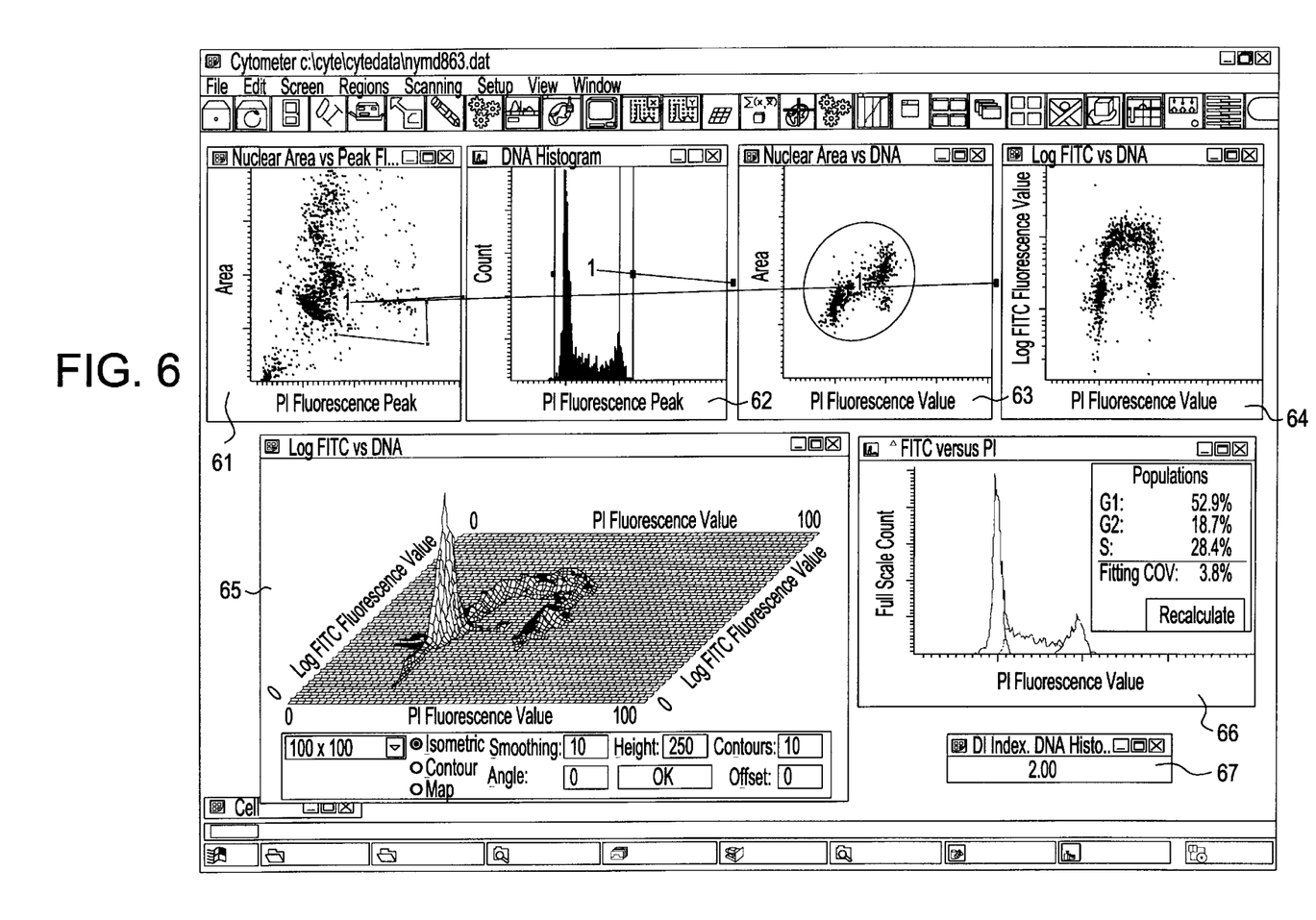
FIG. 6 shows a series of windows on a PC computer monitor screen as each specimen is run.

As each specimen is run, the PC computer monitor screen shows a series of windows such as windows 61–67 shown in FIG. 6. Any number of windows containing scatter diagrams (e.g. 62) of any two features, or histograms (e.g. 61,63,64) of one feature can be displayed (feature ratios can also be used as well). These scattergrams or histograms can be related to the gating region of any other scattergrams or histograms so as to only display cells within the parent display's gating region. Any number of gating regions can be drawn using a mouse. In this way complex relationships involving any sets of features can be developed and used to display subsequent scattergrams or histograms or to select events for relocation and visualization.

In addition to these displays, the laser scanning cytometer can generate isometric displays or contour maps (e.g. 65) of two parameter data. It can compute a variety of statistics of cells within a region, including sub-population counts and distribution statistics (e.g. 66). Cell cycle analyses can also be computed using zero to second degree polynomials or Fast Fourier Transform curve fitting.

Software written for Microsoft Windows, includes the capability to generate, display and print reports with displays, statistics and galleries of cell images inserted dynamically into user designed report forms as data is generated from a specimen. All instrument operating parameters and display setup parameters are stored in user accessible protocol files. All list mode data files include headers describing how the instrument was set up (67). Data files follow the FCS format for compatibility with other analysis software.

As described above, two methods are useful in providing features, one for each of independent assays and dependent assays:

1. Independent Assays:

The laser scanning cytometer is set and used with all of its capabilities to assay a cell specimen, the data from the assay is recorded on computer disk as a list mode file in which, for each cell found, the values for each of a list of features such as total fluorescence at each wavelength range, total amount of scatter, peak values, event area and perimeter and other features, are listed. Along with these features the cytometer software also places in this list for each cell, the X position of the microscope stage to which the slide is affixed, the Y position of the stage, and the scan mirror position, all corresponding to the exact position within the cells' contour of the maximum value of the sensor used for contouring.

The specimen or cytometer is modified for additional scanning or assaying, as described, and the specimen slide is replaced on the microscope stage (if necessary) with the slide holder designed to maintain the original slide position. The specimen is assayed again to create a new list mode file on computer disk storage.

Figure 7:
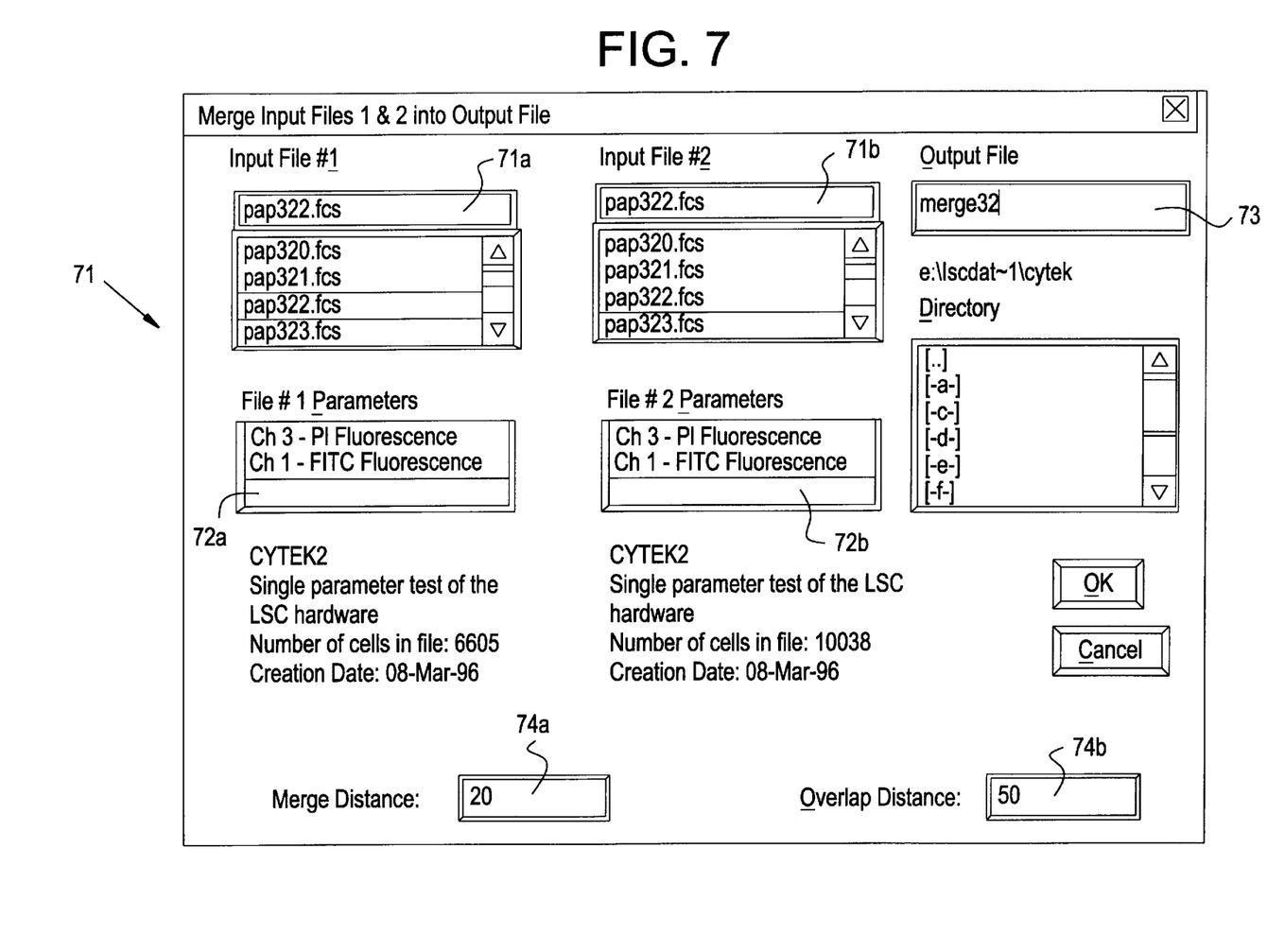
FIG. 7 depicts a monitor screen showing the input files of two screenings of a sample being merged and the output file of the merged data, with merging being effected by cell position.

The two files are then merged with the user identifying the two files to be merged and which information is to be recorded to a merge file. An example of a control window 71 for selectively effecting a file merge is shown in FIG. 7. Input files are identified in windows 71*a* and 71*b* and merge parameters are selected from windows 72*a* and 72*b*. Window 73 indicates merged file identification. Selection is effected by clicking on the selected menu item in the selected windows. A user identifies two files which are to be merged by either using the mouse or by keying in the file names and the user also selects from the menus, data in the files which are to be merged.

Because of some very slight uncertainty between original position and reposition of the specimen slide on the microscope, two distance parameters are utilized in defining a range in which position coordinates are to be considered as defining the position of the same cell. The Merge Distance parameter number, is preset in the controlling software such that whenever the Merge Distance is less than the preset number and the distance between that cell's location and the location of the next nearest neighboring cell found by the cytometer is greater than a number preset for an Overlap Distance parameter, then the indicated cell data parameters are merged into a single file with the combined cell data parameters listed for the merged cell data. This is repeated for the entire file, combining cell data from the two files whenever a match is found. Windows 74*a* and 74*b* indicate the values for the Merge Distance and Overlap Distance used in effecting the merger shown.

The merged cell data is then displayed either in the form of a histogram of the frequency of each of two values of a feature of a sensor, or as a scattergram in which each cell is represented by a dot at coordinates proportional to the values of each of two features of a sensor. Typical sensor features are integrated value, peak value, contour area, etc.

Figure 8A:
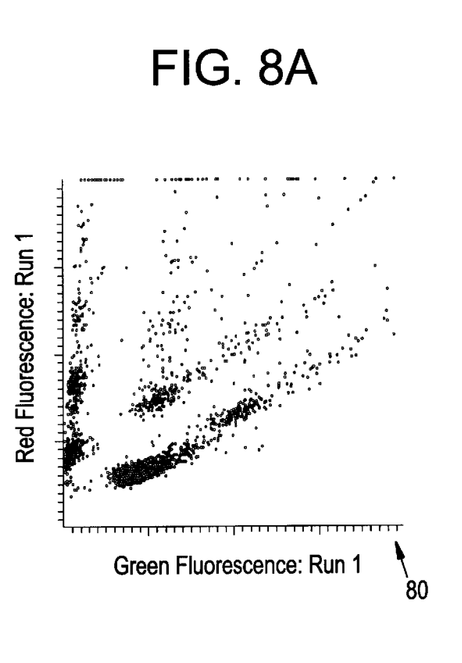
FIGS. 8A–C illustratively depict scattergrams of merged cell data.
Figure 8B:
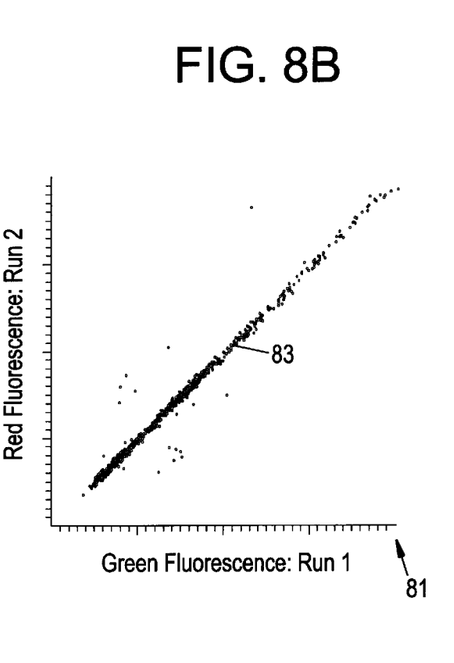
Figure 8C:
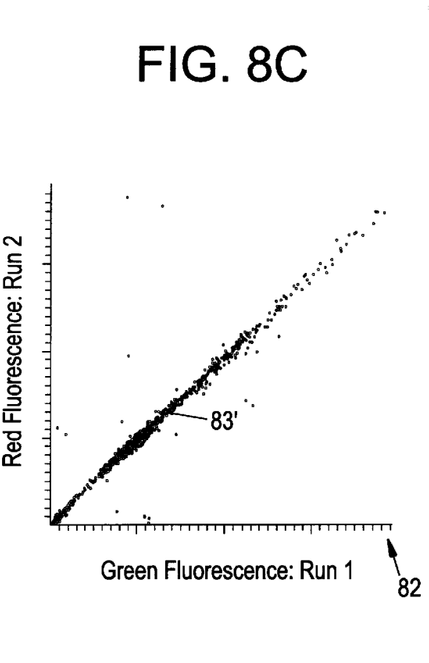

FIGS. 8A–C shows three scattergrams 80, 81, and 82 showing the frequency of cells having values on one axis derived from the feature total fluorescence per cell of one assay versus values on the other axis derived from the feature total fluorescence per cell of a second assay (one assay 81 being red fluorescence, the other 82 green fluoresence). The specimen used for providing the histogram 80 was a mixture of calf thymocytes and chicken blood cells selected so as to provide a wide distribution of measurement values as shown on a scattergram 80. Almost all events fall on the diagonal line 83 and 83', thereby indicating that the cell data is properly matched.

Figure 9:
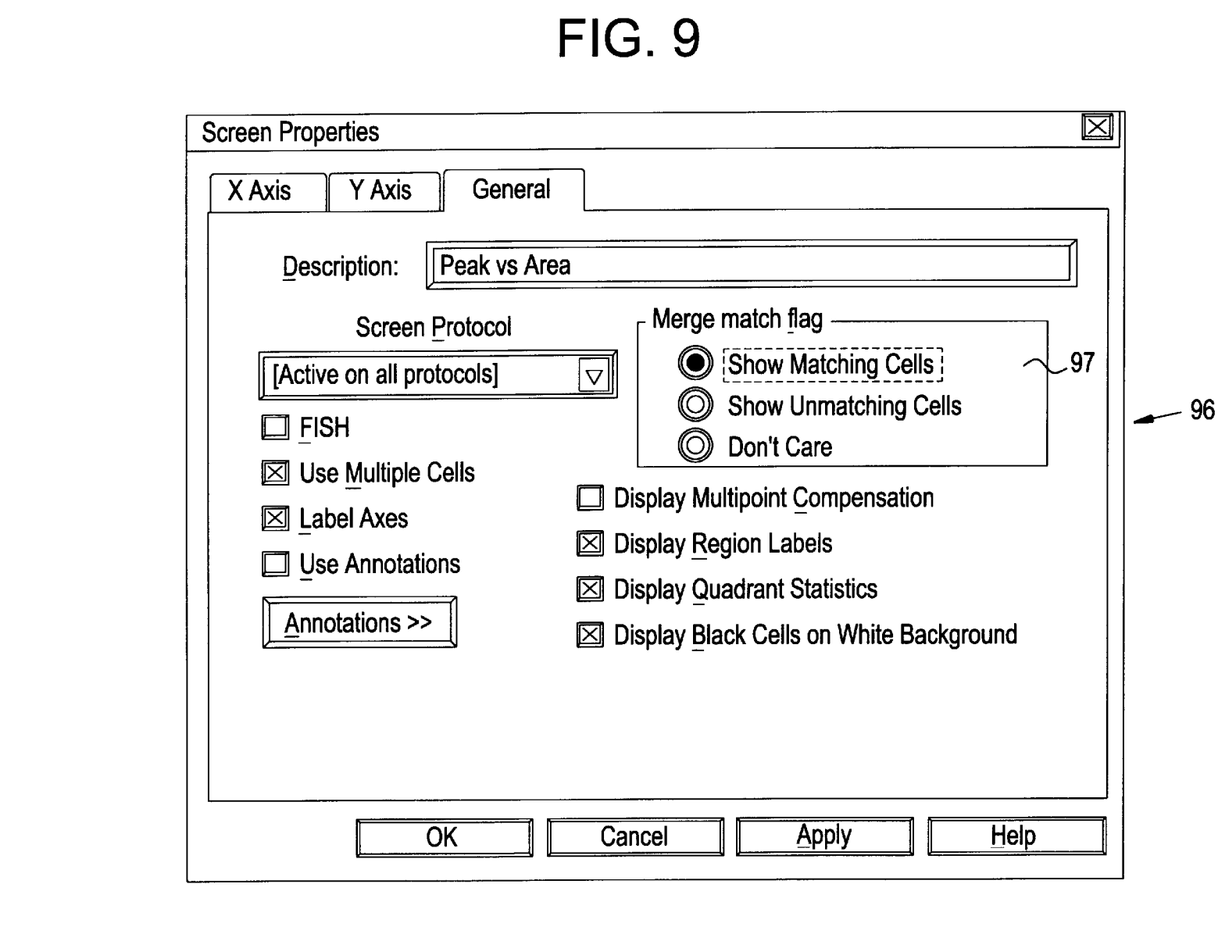
FIG. 9 depicts the monitor screen with general properties of the screened cells in merged and unmerged formats.

Displayed properties of an histogram or a scattergram are selectively controlled by a user such as from a control window display 96 shown in FIG. 9. Such properties include which features of the available sensors are to be displayed, as well as the capability to select data from each assay of a merged file for display, the scale settings and titles and general properties such as properties related to the merged data files, selecting how the user chooses to display merged data files.

The user can select to display events from window 97 in which:
a) there is a match between a cell found in each assay file,
b) those events found in either assay file where is no match with the other file, and
c) all events independent of whether there is a match.

The display screen of the laser scanning cytometer can be utilized to select cells for relocation and viewing by the user using the microscope or a camera, or displays can be used to generate a variety of statistics on cell populations. This is generally done by constructing regions on the display screens surrounding data points of interest and requiring the laser scanning cytometer to relocate cells in these regions or to determine value statistics of data in these regions.

2. Dependent Assays:

In some procedures it is important to determine the position and extent of a cell based on a measurement that will not be available during a second assay. An important example of this is during the use of the dye propidium iodide (PI) which can be specific to the cell constituent, DNA. It is advantageous to use PI, to determine the position of cells, to determine the extent of cell nuclei, and to determine cellular DNA. However, as described above, PI fluorescence is bright and wide in spectral extent and it is difficult to use other dyes which can bind to constituents other than DNA or to nucleic acid specific probes. PI is excited into fluorescence by an Argon ion laser, but not by a red HeNe laser whereas other dyes are red HeNe laser excited. Thus, in order to obtain multiple constituent measurements it is necessary to:

1) stain a specimen with PI and red laser excited dyes to other constituents,
2) assay the specimen using an Argon ion laser scanning a strip through the specimen,
3) in the cytometer software, record the position and a contour surrounding PI fluorescence of each cell found and the cell's DNA value, then
4) assay the scan strip a second time using a red HeNe laser, recording the fluorescence values of the red laser excited dyes within a contour equal in position and size or somewhat bigger than that found for each cell in the first assay.

Figure 10:
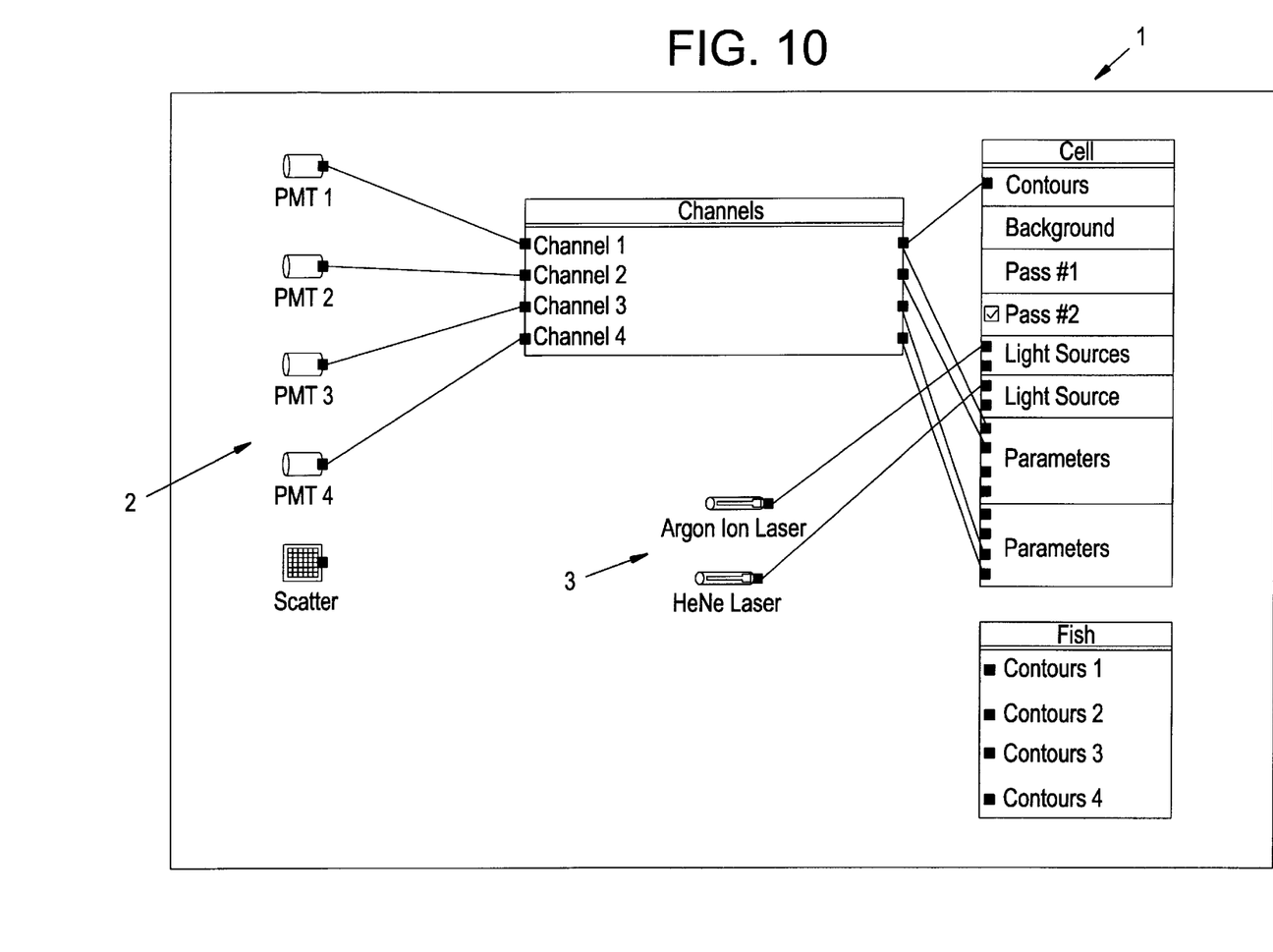
FIG. 10 depicts the monitor screen with selectable parameters for the dual screenings of the cells by laser type, channel, cell parameters, FISH contours and desired output format.

The cytometer software includes the capability to scan strips of the specimen twice, with laser excitation and computational parameters specific for each scan pass. The user selects the parameters of the dual scan assay using the Window shown in FIG. 10. The user configures the sensors and lasers used in each pass by connecting lines between icons representing sensors and lasers and computation algorithms using the computer screen window of FIG. 10. The configuration shown, for example, will use an Argon ion laser on pass one, contour using the first sensor and provide values for two PMT sensors during the first pass. It will rescan each scan strip of the specimen in a second pass, using a red HeNe laser, use the same cell locations and contours of pass 1, but measure fluorescence using two other PMT sensors. Resulting from each pair of strips will be a set of features for each of four different sensors, the first two excited by an Argon ion laser and the second by a HeNe laser.

It is understood that the above discussion with examples of specific embodiments are merely illustrative of the present invention and that changes may be made in scanning parameters, scanning components, measured values, displays, controls, and the like without departing from the scope of the present invention as defined in the following claims.

What is claimed is:

1. A method for scanning a cell sample for analysis, multiple times, with different examination parameters for each of said multiple times, with results of the multiple scannings being merged into a single profile of scanning results for individual cells in the sample, said method comprising the steps of:

a) utilizing scanning means to examine the cell sample and measure examination parameters corresponding to the first of said multiple times, while determining and recording a position of individual cells relative to the scanning means;

b) utilizing the scanning means to examine the cell sample multiple times, with different examination parameters being determined for each of said multiple times, and determining and recording a position of the individual cells relative to the scanning means during each of the multiple times in addition to the different examination parameters; and c) using the recorded cell position of the individual cells from each of the multiple scannings as a key to merge examination results obtained for individual cells during each scan having positions within pre-determined deviation values so as to produce a single profile of scanning results for individual cells in the sample.

2. The method of claim 1, wherein said predetermined deviation values include values of positions outside of a predetermined overlapping distance of individual cells from adjacent cells in the key for merging examination results obtained for individual cells.

3. The method of claim 1, wherein the scanning means comprises a laser scanning cytometer and the cell sample is fixed on support means, whereby the same cells of the cell sample are capable of being examined more than once.

4. The method of claim 3, wherein the support means comprises a microscope slide.

5. The method of claim 4, wherein the determining and recording a position of individual cells relative to the scanning means is effected by computer means, with said computer means merging preselected results obtained for individual cells, having positions within pre-determined deviation values, as being for the same cells.

6. The method of claim 5, wherein individual cell positions are measured and recorded as positions on an X-axis and a Y-axis, relative to a longitudinal plane of the microscope slide and a position relative to a scan mirror of the laser scanning cytometer, in a direction normal to the longitudinal plane.

7. The method of claim 6, wherein the cells are stained with at least one fluorescent dye and wherein the individual cells are fluorescence contoured by pre-setting sensors in the laser scanning cytometer to measure individual position fluorescence values within each cell and to locate pixel positions within each cell where there is a predetermined threshhold value drop-off of fluorescence value adjacent thereto, wherein a position having the predetermined threshhold value drop-off comprises a boundary position, with a sum of such boundary positions working to contour each cell, and wherein said positions within predetermined deviation values are measured from the contour of the individual cells.

8. The method of claim 7, wherein said single profile is made to comprise any of simultaneous characterizion of DNA per cell, cell proliferation, and cell apoptosis.

9. The method of claim 7, wherein any one of kinetic properties of heterogeneous populations of cells and per cell differences between a control and an analyte of the cells are measured and recorded between said multiple scannings.

10. The method of claim 7, wherein the multiple scannings are made with adjustment of computational parameters of the laser scanning cytometer by any one of, changing a gain of sensors to determine both large and small amounts of a constituent with great dynamic range using limited dynamic range sensor amplifiers, and by changing a size of said contours to better measure cellular constituent distributions.

11. The method of claim 7, wherein the cell sample is also examined either without staining or with a control stain of an irrelevant antibody conjugated to a fluorescent dye, prior to said staining of the cells with at least one fluorescent dye.

12. The method of claim 7, wherein propidium iodide is used to stain the cells and used to determine:

a) a position of cells, b) an extent of cell nuclei, and c) cellular DNA, wherein the cell sample is stained with propidium iodide and red laser excited dyes, and wherein the cell sample is first scanned with an Argon ion laser scanning a strip through the sample, and a position and contour surrounding propidium iodide fluorescence of each cell in addition to a DNA value of each cell is recorded, and thereafter the cell sample is examined with the scan strip a second time using a red HeNe laser, and fluorescence values of the red laser excited dyes are recorded within a contour equal in position and at least equal in size to that found for each cell in the first scan.

13. The method of claim 5, wherein the merged results are transformed into any one of a histogram, scattergram and contour map.

14. The method of claim 3, wherein the cell sample is stained with at least two different fluorescent dyes which fluoresce upon impingement thereof of laser light of different wavelength respectively, and wherein one examination of the cell sample is with laser light of a wavelength which causes fluorescing of one of said different fluorescent dyes and wherein at least one other examination of the cell sample is with laser light of a wavelength which causes fluorescing of another of said different fluorescent dyes.

15. The method of claim 14, wherein one of said at least two different fluorescent dyes comprises a red fluorescent dye and another of said at least two different fluorescent dyes comprises a green fluorescent dye and wherein an Argon laser is used to provide laser light which causes fluorescing of the green fluorescent dye and an HeNe laser is used to provide laser light which causes fluorescing of the red fluorescent dye.

16. The method of claim 14, wherein one fluorescent dye is selected from the group consisting of propidium iodide and fluorescein, and wherein another fluorescent dye is selected from the group consisting of CY3 and CY5.

* * * * *